United States Patent [19]

Straus

[11] 4,094,888
[45] June 13, 1978

[54] MALEIC ANHYDRIDE PROCESS

[75] Inventor: Alan E. Straus, El Cerrito, Calif.

[73] Assignee: Chevron Research Company, San Francisco, Calif.

[21] Appl. No.: 580,443

[22] Filed: May 23, 1975

[51] Int. Cl.² .................................... C07D 307/60
[52] U.S. Cl. ......................................... 260/346.75
[58] Field of Search ................................ 260/346.8

[56] References Cited

U.S. PATENT DOCUMENTS

| | | | |
|---|---|---|---|
| 3,864,280 | 2/1975 | Schneider | 260/346.8 |
| 3,904,652 | 9/1975 | Frank | 260/346.8 |
| 3,907,833 | 9/1975 | Slinkard et al. | 260/346.8 |

OTHER PUBLICATIONS

Paraffins, Chemistry & Technology, Asinger, p. 26, Pergamon Press (1968).

Primary Examiner—Henry R. Jiles
Assistant Examiner—Bernard Dentz
Attorney, Agent, or Firm—D. A. Newell; John Stoner, Jr.; W. Keith Turner

[57] ABSTRACT

A process for the catalytic production of maleic anhydride from n-butane with sustained high activity for the catalyst which comprises contacting the n-butane feed with oxygen gas and a catalyst comprising oxides of vanadium and phosphorus and maintaining between 0.5 and 50 mole percent propane in the feed, based on propane plus n-butane, during the normal onstream time.

6 Claims, No Drawings

MALEIC ANHYDRIDE PROCESS

BACKGROUND OF THE INVENTION

The present invention relates to an improved catalytic hydrocarbon oxidation process to obtain maleic anhydride from butane.

Catalysts for use in oxidation of hydrocarbons are well known and the production of dicarboxylic acid anhydrides by vapor-phase catalytic oxidation is well known. Suitable processing conditions for the use of these catalysts in oxidation processes such as partial oxidation processes to convert benzene, butene, butane, and other hydrocarbons to maleic anhydride are also well known.

A series of patents to Kerr, including U.S. Patents 3,156,705; 3,156,706; 3,156,707; 3,238,254; 3,255,211; 3,255,212; 3,255,213; 3,288,721; 3,351,565; and 3,385,796 disclose phosphorus-vanadium oxide catalysts for vapor-phase oxidation of butene to maleic anhydride. For example, Kerr U.S. Pat. No. 3,156,705 discloses a catalyst comprising phosphorus and vanadium oxides wherein an additional component is included in the catalyst as a phosphorus stabilizer, which stabilizer is said to improve the life of the catalyst.

The Kerr references suggest the use of catalysts with a surface area below 5 $m^2/g$. Thus Kerr U.S. Pat. No. 3,288,721 states at columm 5, lines 12-16:

"The catalyst support, if used, provides not only the required surface for the catalyst, but gives physical strength and stability to the catalyst material. The carrier or support normally has a low surface area, as usually measured from about 0.001 to about 5 square meters per gram."

The suggestion of low surface area for the hydrocarbon oxidation catalyst is consistent with other prior art, which suggests the use of low surface area catalyst for hydrocarbon oxidation catalysts. Thus, in an article by C. F. Cullis, entitled "Heterogenous Catalytic Oxidation of Hydrocarbons" (Ind. & Eng. Chem. 59 [12] 18 (1967)), on page 21 it is stated: "...the best oxidation catalysts have large diameter pores and are generally of fairly low surface area." By "hydrocarbon oxidation catalysts" it should be understood that reference is to catalysts for the partial rather than complete oxidation of hydrocarbons all the way to carbon oxides.

Bergman U.S. Pat. No. 3,293,268 discloses a vanadium-phosphorus oxide catalyst for butane oxidation to maleic anhydride.

U.S. Pat. No. 3,846,280 to Schneider discloses a catalyst comprising vanadium-phosphorus oxides for use in catalytic oxidation of hydrocarbons, such as butane, to maleic anhydride. The catalysts used in the Schneider process have a relatively high surface area, preferably above 7 square meters per gram.

Defensive Publication No. 784,946 describes reactivation of oxidation catalysts which have been exposed to excessive heat. The catalysts—for example, ammoxidation catalysts—are reactivated using a reducing gas such as propylene.

U.S. Pat. No. 1,896,031 discloses reactivation of an oxidation catalyst using a reducing gas; the reducing gas of Example 1 being 3% toluene, 15% air, 2% ammonia and 80% coal gas.

U.S. Pat. No. 2,500,776 discloses reactivation of an ammoxidation catalyst using high-temperature hydrogen.

Netherlands Patent Application No. 73/14746 is directed to an improvement in a process for the preparation of maleic anhydride wherein n-butane is oxidized with a gas containing molecular oxygen in the presence of a phosphorus-vanadium-oxygen complex catalyst and wherein the catalyst deactivates under conditions of high temperature. According to Netherlands 73/14746 the activity of the deactivated catalyst is restored by periodically contacting the catalyst with a reducing agent. Reducing agents disclosed are hydrogen, methane, carbon monoxide and hydrogen sulfide gases.

SUMMARY OF THE INVENTION

According to the present invention, a process is provided for the catalytic production of maleic anhydride from n-butane with sustained high activity for the catalyst which comprises contacting the n-butane feed with oxygen gas and a catalyst comprising oxides of vanadium and phosphorus and maintaining between 0.5 and 50 mole percent propane in the feed, based on propane plus n-butane, during the normal on-stream time.

Preferably the amount of propane is at least one mole percent, and higher mole percents, such as 3 to 50 mole percent or even 10 to 50 mole percent, are still further preferred. It is to be understood that the propane is present in the feed substantially continuously during the on-stream time, which on-stream time may range up to 1,000 or even 5,000 or 15,000 hours before the catalyst is replaced or rejuvenated. The feed to the process may for a short period of time be altered such that the required propane content is not present while still practicing the spirit of the present invention.

Among other factors, the present invention is based on my finding that the activity of a catalyst used in the oxidation of normal butane to maleic anhydride, comprising vanadium and phosphorus oxides, can be maintained at an unexpectedly higher level by diluting the butane feed with propane as opposed to a similar process where the feed is not diluted with propane. This finding is advantageously used in situations where heretofore it would have been assumed desirable to separate propane substantially entirely from $C_4$ feeds, such as refinery off-gas streams and fuel gas streams containing both propane and butane. Reference herein to butane is to be understood to mean normal butane unless otherwise indicated.

In addition to the use of propane in the butane feed, preferred process conditions include a reaction zone temperature between 300° and 500° C. Other operating conditions as described in commonly assigned Ser. No. 359,294 now U.S. Pat. No. 4017521, such as space velocity and pressure, are preferred for use in the present process: the disclosure of Ser. No. 359,294 is incorporated herein by reference.

The present invention is especially advantageously employed with catalysts of the type described in Schneider U.S. Pat. No. 3,864,280, the disclosure of which patent is incorporated herein by reference. Thus, preferred catalysts are phosphorus-vanadium mixed oxides containing pentavalent phosphorus, vanadium and oxygen, the vanadium having an average valence in the range from about plus 3.9 to plus 4.6 and the oxide having a phosphorus to vanadium atomic ratio in the range from about 0.9-1.8 to 1, with an intrinsic surface area in the range from about 7 to 50 square meters per gram.

More preferred catalysts are those in which the vanadium has an average valence in the range from about 4.1 to 4.4, the phosphorus to vanadium atomic ratio is in the range 1.0–1.5 to 1, and the intrinsic surface area is in the range 10 to 50 square meters per gram.

Crystals having the B-Phase structure exhibit a characteristic powder x-ray diffraction pattern (CuKα) as listed in Table I below:

TABLE I

| d (Angstrom) | Line Position 2θ, Degrees | Intensity, I |
| --- | --- | --- |
| 6.3 | 14.2 | 10 |
| 4.8 | 18.5 | 7 |
| 3.9 | 23.0 | 100 |
| 3.13 | 28.5 | 58 |
| 2.98 | 30.0 | 29 |
| 2.65 | 33.8 | 7 |

The dimensions of the unit cell for B-phase, as obtained from the complete powder x-ray diffraction data, are $a = b = 19.2$ Å and $C = 7.8$ Å. The crystalline phase is of hexagonal structure.

EXAMPLES

In these examples the reactor used was a ⅜ inch i.d. pyrex tube, 24 inches long and contained 14 inches of catalyst pellets. A ⅛ inch thermowell in the center of the tube contained a movable thermocouple. A mixture of 1.5% hydrocarbon in air was fed at a volume hourly space velocity (VHSV) of 750 V/V/hr at S.T.P. and the off-gas was bubbled through a water scrubber which was then titrated for maleic acid. Temperature was controlled to give n-butane conversion between 80 and 90%.

Catalyst activity is expressed as relative first order rate constant, K, corrected to 800° F average bed temperature, and calibrated as follows:

$$K = \frac{\frac{T}{535}}{\frac{P}{14.7}} \times VHSV \times \ln\left[\frac{1}{1-x}\right]$$

T = Average bed temperature (°R)
P = Average bed pressure (psia)
VHSV = Volume hourly space velocity $$= \frac{\text{Volume of feed gas (75° F., 1 atm)}}{\text{Volume of rector bed} \times \text{hr.}}$$

x = Mole fraction n-butane reacted The K at the reaction temperature is then corrected to 800° F by the following equation:

$$K_{800} = K_T e^A \text{ in which } A = 16.54\left[\frac{1260 - T}{T}\right]$$

Values of $K_{800}$ in excess of 2000 are considered satisfactory. For completely satisfactory catalysts it is necessary that, in addition to having high activities (K values), they must also convert a substantial amount of the feed stock to product. That is, they must have high selectivity for producing the desired product. Such selectivities are measured as the moles of product produced per mole of reactant consumed, usually expressed as mole percent.

TABLE II

| Run No. | Hrs on Stream | Feed, mole-% n-butane | Feed, mole-% Propane | Avg T,° F | $K_{800}$ | Conv, % | Select, mole-% |
| --- | --- | --- | --- | --- | --- | --- | --- |
| 1 | 451–499 | 100 | 0 | 766 | 5030 | 84 | 67 |
| 2 | 788–866 | 50 | 50 | 711 | 9030 | 81 | 69 |
| 3 | 957–963 | 100 | 0 | 753 | 6730 | 86 | 62 |
| 4 | 1291–1506 | 100 | 0 | 752 | 5050 | 81 | 70 |
| 5 | 1511–1531 | 50 | 50 | 738 | 9200 | 88 | — |
| 6 | 1534–1602 | 100 | 0 | 766 | 6040 | 89 | 63 |
| 7 | 1609–1701 | 80 | 20 | 759 | 6750 | 89 | 61 |
| 8 | 1771–1871 | 100 | 0 | 756 | 6350 | 85 | — |

The runs 2, 5 and 7 summarized in Table II illustrate the process of the present invention and show that surprisingly good activity and conversion are attained when feeding both butane and propane to the reactor. The catalyst used was prepared in accordance with the method disclosed and claimed in commonly assigned patent application Ser. No. 729,920, the disclosure of which application is incorporated herein by reference.

I claim:

1. A process for the catalytic production of maleic anhydride from n-butane with sustained high activity for the catalyst which comprises contacting the n-butane feed with oxygen gas and a catalyst comprising oxides of vanadium and phosphorus and maintaining between 3 and 50 mole percent propane in the feed, based on propane plus n-butane, during the normal on-stream time.

2. A process in accordance with claim 1 wherein the propane is at least 10 mole percent.

3. A process in accordance with claim 1 wherein the temperature is between 300° and 500° C.

4. A process in accordance with claim 1 wherein said catalyst is a phosphorus-vanadium mixed oxide containing pentavalent phosphorus, vanadium and oxygen, said vanadium having an average valence in the range from about plus 3.9 to plus 4.6, said oxide having a phosphorus to vanadium atomic ratio in the range from about 0.9–1.8 to 1, and an intrinsic surface area in the range from about 7 to 50 square meters per gram.

5. A process in accordance with claim 4 wherein
 (a) the average valence of the vanadium is in the range from about 4.1 to 4.4;
 (b) the phosphorus to vanadium atomic ratio is in the range 1.0–1.5 to 1; and
 (c) the intrinsic surface area is in the range 10 to 50 square meters per gram.

6. A process in accordance with claim 4 wherein the catalyst has a B-phase content in excess of about 25 weight percent.

* * * * *

UNITED STATES PATENT AND TRADEMARK OFFICE
CERTIFICATE OF CORRECTION

PATENT NO. : 4,094,888
DATED : June 13, 1978
INVENTOR(S) : Alan E. Straus

It is certified that error appears in the above—identified patent and that said Letters Patent are hereby corrected as shown below:

Column 3, line 63, "rector bed x hr." should read --reactor bed x hr.--

Signed and Sealed this

Nineteenth Day of December 1978

[SEAL]

Attest:

RUTH C. MASON
Attesting Officer

DONALD W. BANNER
Commissioner of Patents and Trademarks